(12) United States Patent
Batthyány et al.

(10) Patent No.: US 12,416,971 B2
(45) Date of Patent: Sep. 16, 2025

(54) COMPUTER IMPLEMENTED METHOD, A DEVICE AND A SYSTEM

(71) Applicant: XRSynergies GmbH, Vienna (AT)

(72) Inventors: Marie-Isabelle Batthyány, Vienna (AT); Till Gaston Balz Bay, Zürich (CH); Christoph Krautz, Zürich (CH)

(73) Assignee: XRSynergies GmbH, Vienna (AT)

( * ) Notice: Subject to any disclaimer, the term of this patent is extended or adjusted under 35 U.S.C. 154(b) by 2 days.

(21) Appl. No.: 18/612,271

(22) Filed: Mar. 21, 2024

(65) Prior Publication Data
US 2024/0319788 A1    Sep. 26, 2024

(30) Foreign Application Priority Data

Mar. 21, 2023 (GB) ..................................... 2304107

(51) Int. Cl.
*G06F 3/01*    (2006.01)
(52) U.S. Cl.
CPC .................... *G06F 3/013* (2013.01)
(58) Field of Classification Search
CPC . G06F 3/011–013; G16H 40/63; G16H 40/67
See application file for complete search history.

(56) References Cited

U.S. PATENT DOCUMENTS

| | | | | |
|---|---|---|---|---|
| 9,703,373 B2* | 7/2017 | Kohlhoff | ................ | G06V 40/19 |
| 10,121,355 B1* | 11/2018 | Mossoba | ................ | G06V 20/20 |
| 11,308,629 B2* | 4/2022 | Edell | ................ | G06T 7/20 |
| 11,501,875 B1 | 11/2022 | Kloster et al. | | |
| 11,698,677 B1* | 7/2023 | Chiu | ................ | G06F 3/14 |
| | | | | 345/629 |
| 2014/0253437 A1 | 9/2014 | Vaught et al. | | |
| 2015/0309569 A1* | 10/2015 | Kohlhoff | ................ | G06V 40/193 |
| | | | | 382/103 |
| 2018/0102186 A1 | 4/2018 | Jarvisalo et al. | | |
| 2019/0034706 A1* | 1/2019 | el Kaliouby | ....... | H04N 21/4223 |
| 2019/0102706 A1 | 4/2019 | Frank et al. | | |
| 2019/0294239 A1* | 9/2019 | Suzuki | ................ | G02B 27/0179 |
| 2021/0065378 A1* | 3/2021 | Edell | ................ | G06N 3/08 |
| 2023/0333641 A1* | 10/2023 | Boesel | ................ | G02B 27/0172 |

(Continued)

OTHER PUBLICATIONS

Wilson et al., "A new metric for grey-scale image comparison", Department of Mathematics, UWA, 1995, 22 pages.

(Continued)

*Primary Examiner* — Patrick F Marinelli
(74) *Attorney, Agent, or Firm* — Dority & Manning, P.A.

(57) ABSTRACT

A computer-implemented method of determining whether digital content has been viewed by a subject, the method including, displaying, by a display device, the digital content to the subject; tracking the gaze of the subject whilst displaying at least a temporal portion of the digital content to acquire tracking data; determining from the tracking data, the display portions of the display device viewed in that temporal portion of the digital content; and generating at least one score by comparing these portions to a predetermined template of display portions for that temporal portion of the digital content; and determining that the subject has viewed at least the temporal portion of the digital content based on the at least one score. A display device and system are also disclosed.

17 Claims, 9 Drawing Sheets

(56) References Cited

U.S. PATENT DOCUMENTS

| | | | |
|---|---|---|---|
| 2023/0333642 A1* | 10/2023 | Chimalamarri | G06F 3/013 |
| 2023/0333643 A1* | 10/2023 | Schmidtchen | G06F 3/017 |
| 2024/0302898 A1* | 9/2024 | Schmidtchen | G06F 3/011 |
| 2024/0319788 A1* | 9/2024 | Batthyány | G16H 40/67 |
| 2025/0014204 A1* | 1/2025 | Srivastava | H04N 21/2187 |

OTHER PUBLICATIONS

UK Combined Search and Examination Report for corresponding Application No. GB2304107.2, dated Sep. 8, 2023, 6 page.

* cited by examiner

COMPUTER IMPLEMENTED METHOD, A DEVICE AND A SYSTEM

CROSS-REFERENCE TO RELATED APPLICATIONS

The present application is based upon and claims the right of priority to GB Patent Application Number 2304107.2, filed Mar. 21, 2023, the disclosure of which is hereby incorporated by reference herein in its entirety for all purposes.

TECHNICAL FIELD

The present invention relates to a device, system and computer-implemented method for determining whether digital content has been viewed by a subject. More particularly, the invention provides a technique based on gaze tracking from which an objective measure representative of the subject having viewed the digital content can be determined.

BACKGROUND

There are many situations where information must be conveyed to a subject person, and for various reasons, for example, safety reasons, or legal reasons, it is necessary to ensure that the subject person has properly engaged with the content material, and where an assessment as to whether that person has properly reviewed the information. For example, in medical consent scenarios. Conventionally, a patient consents to a medical procedure based on an explanation of that medical procedure provided by a clinician. A problem with such an approach is that there is no objective measure from which it can be deduced whether a patient has properly viewed the medical procedure. Accordingly, patients end up consenting to a medical procedure, which they have not properly understood.

U.S. Pat. No. 11,501,875 B2 discloses a method for obtaining informed consent of a patient for a medical procedure. In the method, a video describing the medical procedure is displayed to the patient in a first display portion of a device, and an image of the patient, captured whilst the patient watches that video, is displayed in a second display portion of the device. The entire display is recorded for demonstrating that the patient has watched the video.

US 2018/0102186 A1 discloses a method for managing an electronic informed consent process in a clinical trial, which includes tracking the time the participant spends reading content, and comparing the time spent on reading the content is compared with a pre-defined expected time for reading the content, A deviation in the time spent is detected if the difference between the time spent and the predefined expected time does not meet a time difference threshold. The method includes triggering an action to mitigate impact of the deviation on the electronic informed consent. In an example, each section of the consent form is compared against a time expected for that section. An alert is triggered if the deviation between these times does not meet a time difference threshold. Eye-tracking is mentioned in the context of determining a reason why a deviation in the time spent is determined. The time spent is tracked either by web tracking or content tracking (the content includes analytics code which tracks events performed by the patient).

SUMMARY

The invention provides a computer-implemented method of determining whether digital content has been viewed by a subject, the method comprising, displaying, by a display device, the digital content to the subject; tracking the gaze of the subject whilst displaying at least a temporal portion of the digital content to acquire tracking data; determining from the tracking data, the display portions of the display device viewed in that temporal portion of the digital content; and generating at least one score by comparing these portions to a predetermined template of display portions for that temporal portion of the digital content; and determining that the subject has viewed at least the temporal portion of the digital content based on the at least one score.

Determining from the tracking data the display portions, may comprise determining the display portions for each of multiple time points within the time period (i.e. the temporal portion).

Generating a score by comparing may comprise comparing at least a plurality of time points of the acquired tracking data with the corresponding points of the predetermined template.

The method may further comprise generating the predetermined template by tracking a gaze of at least one model subject whilst displaying said digital content and acquiring the gaze tracking data.

The acquired tracking data may comprise positional data related to the subject's gaze for each of a plurality of timestamped points. Generating a score may comprise calculating an error value for each time stamped point by comparing the positional information at each timestamped point with corresponding positional data from the predetermined template. Generating the score may comprise calculating a cost value based on the size of the error value. The method may also comprise generating, for each cost value, a bounded score. The score or bounded score can relate to the digital content as a whole or for a temporal portion thereof.

In the method, positional information related to the subject's gaze that has been acquired at particular time points can be discarded if there is no corresponding positional information at the same time points in the predetermined template.

In the method, the cost value may be transformed into a bounded value using a sigmoid function. The sigmoid function may be as shown in Equation 3. Advantageously, the tuning value for the sigmoid function can be determined based on a cost value calculated for a model subject that has been instructed, prior to viewing the digital content, to not view the digital content attentively. As the chance of a model subject viewing digital content attentively, when they have been told not to, is low, the accuracy of determining if a test subject has viewed the digital content attentively can be improved.

The method may further comprise transmitting, by a server, instructions to the display device to display the digital content responsive to the server receiving a first identifier defining the subject and a second identifier defining the display device, the method optionally further comprising: transmitting, by the server, the digital content to the display device. The method may further comprise, before the digital content is displayed by the display device, the steps of, selecting the display device for displaying the digital content; scanning, by a subject device, a code provided on the display device, the code comprising or encoding the second identifier; and transmitting, by the subject device, the second identifier to the server.

The method may further comprise, before the first identifier is transmitted to the display device, the steps of, generating the first identifier; associating the digital content to the first identifier; and transmitting the first identifier and at least the association between the digital content and first identifier to the server for storage.

The display device may be a virtual-reality, VR, headset, augmented-reality, AR, headset, or an extended-reality, XR, headset, and the gaze of the subject is tracked using sensors built into the VR, AR, or XR headset.

Conditional upon the score being greater than a predetermined threshold, the method may comprise certifying that the subject is competent to consent to a process to which the digital content relates. The process may be a medical procedure.

Conditional upon the score being greater than a predetermined threshold, the method may comprise certifying that the subject has successfully completed at least part of a training course to which the digital content relates.

The invention also provides a display device comprising: a network interface for establishing wireless connections; at least one processor coupled to the network interface; and a memory storing executable instructions, wherein the executable instructions are configured to manipulate at least one processor so that the method of the invention can be performed.

The invention also provides a system, comprising: a server, comprising a network interface; at least one processor coupled to the network interface; and a memory storing executable instructions, wherein the executable instructions are configured to manipulate the at least one processor so that the method of the invention can be performed.

The invention also provides a system. The system comprises a server and a display device. The server comprises a network interface for establishing network connections; at least one processor coupled to the network interface; and a memory storing executable instructions, wherein the executable instructions are configured to manipulate the at least one processor to cause the method of the invention to be performed. The display device comprises a network interface for establishing network connections; at least one processor coupled to the network interface; and a memory storing executable instructions, wherein the executable instructions are configured to manipulate the at least one processor to cause the method of the invention to be performed.

The invention further comprises a computer program that when run on a computer, causes the computer to perform the method of the invention.

BRIEF DESCRIPTION OF THE DRAWINGS

Embodiments of the invention will now be described in detail with reference to the drawings, in which.

DETAILED DESCRIPTION

The present disclosure relates to a device, system for, and method of, determining whether digital content has been viewed by a subject. In particular, the disclosure provides a technique based on gaze tracking from which an objective measure representative of the subject having viewed the digital content can be determined. Various methods and means for gaze tracking are known and are within the scope of the present disclosure. A brief introduction to gaze tracking can be found at https://www.tobiidynavox.com/pages/what-is-eye-tracking, which is incorporated by reference.

In the method, digital content is displayed to a subject and their gaze is tracked during this display. Using this information, the display portions of the display device viewed by the subject are determined. The display portions viewed can be stored in a map representing the subject's gaze over the duration of the digital content. This map is then compared with a predetermined template for that digital content and a score is generated based on the similarity between them. The predetermined template is a map of an average or "model" subject's gaze over the duration of the digital content, which has been determined to be representative of the subject having viewed the digital content. The subject is determined to have viewed the digital content conditional upon this similarity score being greater than a predefined threshold.

Figure 1:
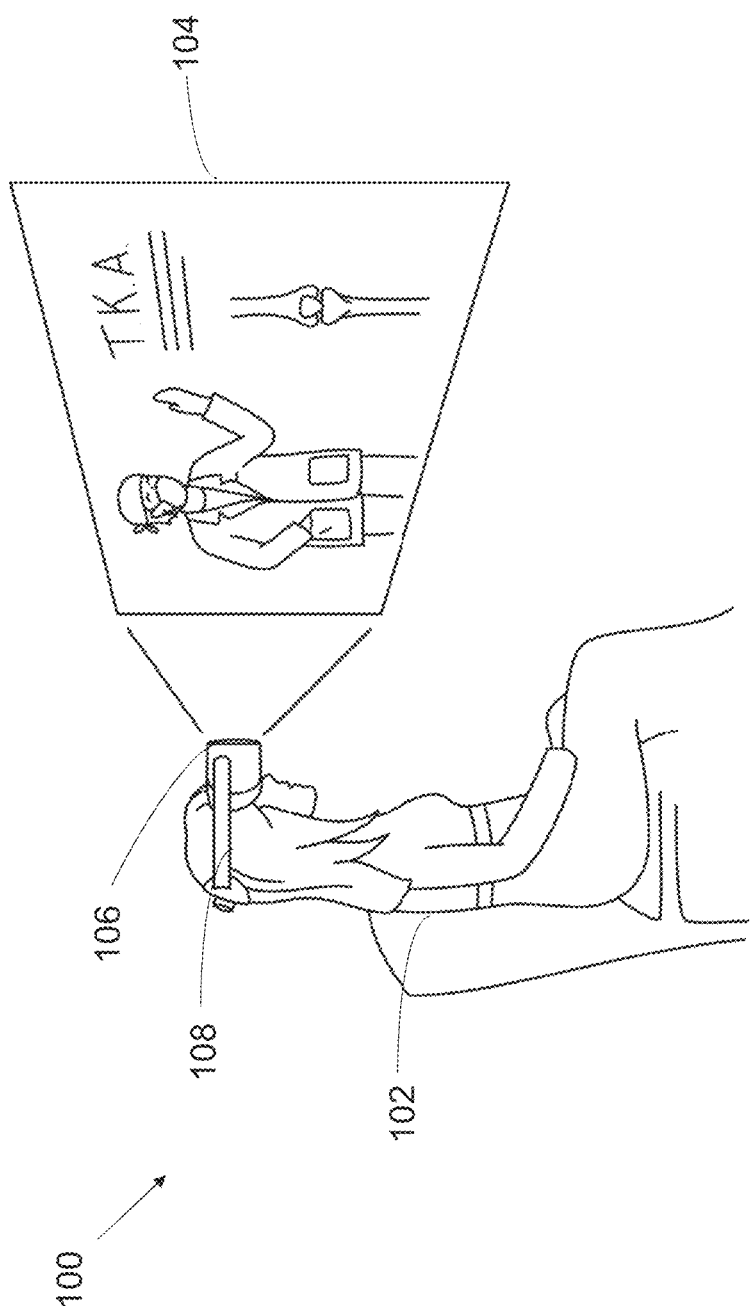
FIG. 1 is a schematic illustration of a subject viewing digital content.

FIG. 1 is a schematic illustration of a system 100 for explaining aspects of the invention. A subject 102 views digital content 104 displayed in a virtual reality (VR) headset 106. The digital content is in the form of a video. Other forms of digital content, for example, still images, a slide show with or without audio content, are however possible. In FIG. 1, a projection of the digital content is shown for illustrative purposes only. The skilled reader will understand that the digital content is displayed in a display screen on the VR headset. The VR headset is mounted to the subject via a fastening element 108, such as a head strap.

Figure 2:
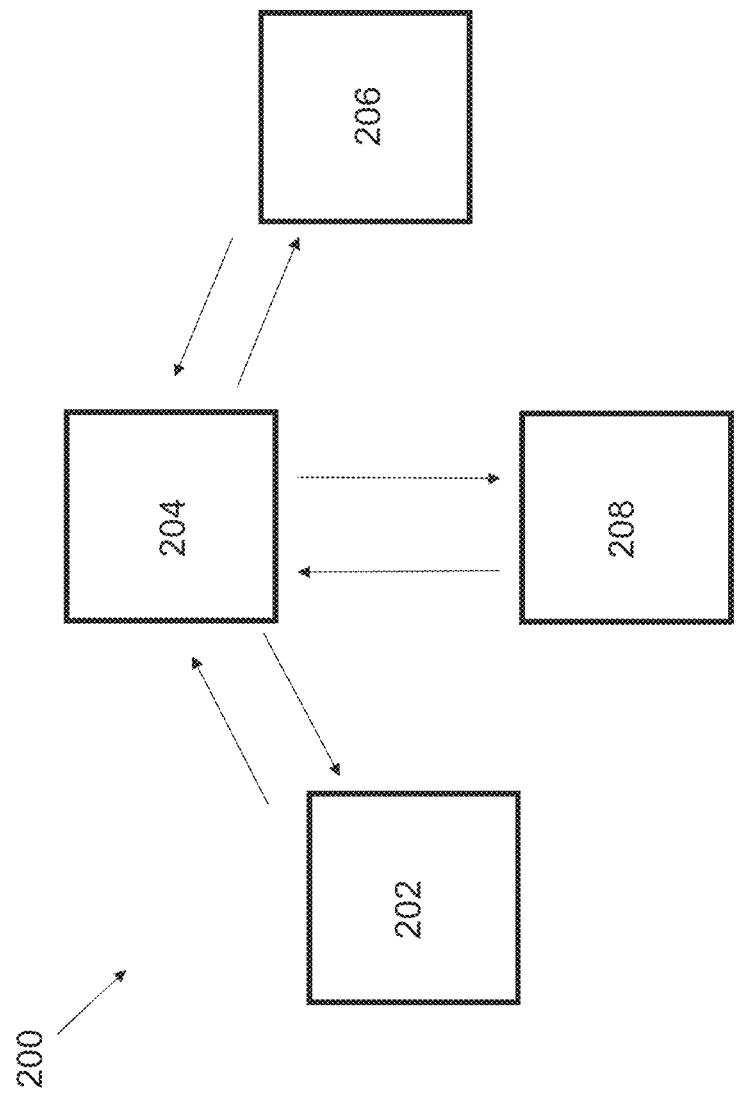
FIG. 2 is a schematic illustration indicating the flow of digital information in a system.

FIG. 2 is a schematic diagram indicating the flow of digital information in a system 200. The system comprises a display device 202, a server 204, an administrator device 206, and a user device 208. The administrator device 206 and user device 208 may be the same device, which may be termed, generally, a user device, an administrator device, or an operator device. Also, there may be multiple user devices. The user device 208 and administrator device 206 may be constituted by a mobile phone, tablet, computer or the like. As will be understood by the skilled person, the functions of the administrator and user devices may be performed by different devices by communication with the server 204, for example by running a same application (app)—ether locally or as a web app. Other devices may be connected to the server, such as supervisor devices. It is contemplated, in particular, that the system can comprise a plurality of display devices.

Each of the display device 202, server 204, administrator device 206, and user device 208 includes a network interface for establishing wireless connections (e.g., cellular, Wi-Fi, etc.), at least one processor coupled to the network interface, and a memory storing executable instructions. The executable instructions are configured to manipulate at least one processor such that at least one processor performs certain method steps. The method steps, and in particular which of these devices performs a particular step, are described below in relation to FIGS. 3, 7 and 8.

More generally, the system 200 provides a platform for facilitating a process for pairing a display device to a particular subject, configuring digital content on the display device for displaying to that subject, and determining, using objective measures, whether that subject has viewed the digital content. The results of the determination can be stored at the server 204, which serves as a repository for storing data. Such data can be uploaded to or downloaded by the administrator or user device 208 using a web-based application. Example data that can be stored includes: IDs, the association of these IDs to digital content, the digital content, and the results from FIG. 3 (e.g., the map, first and second scores).

Figure 8:
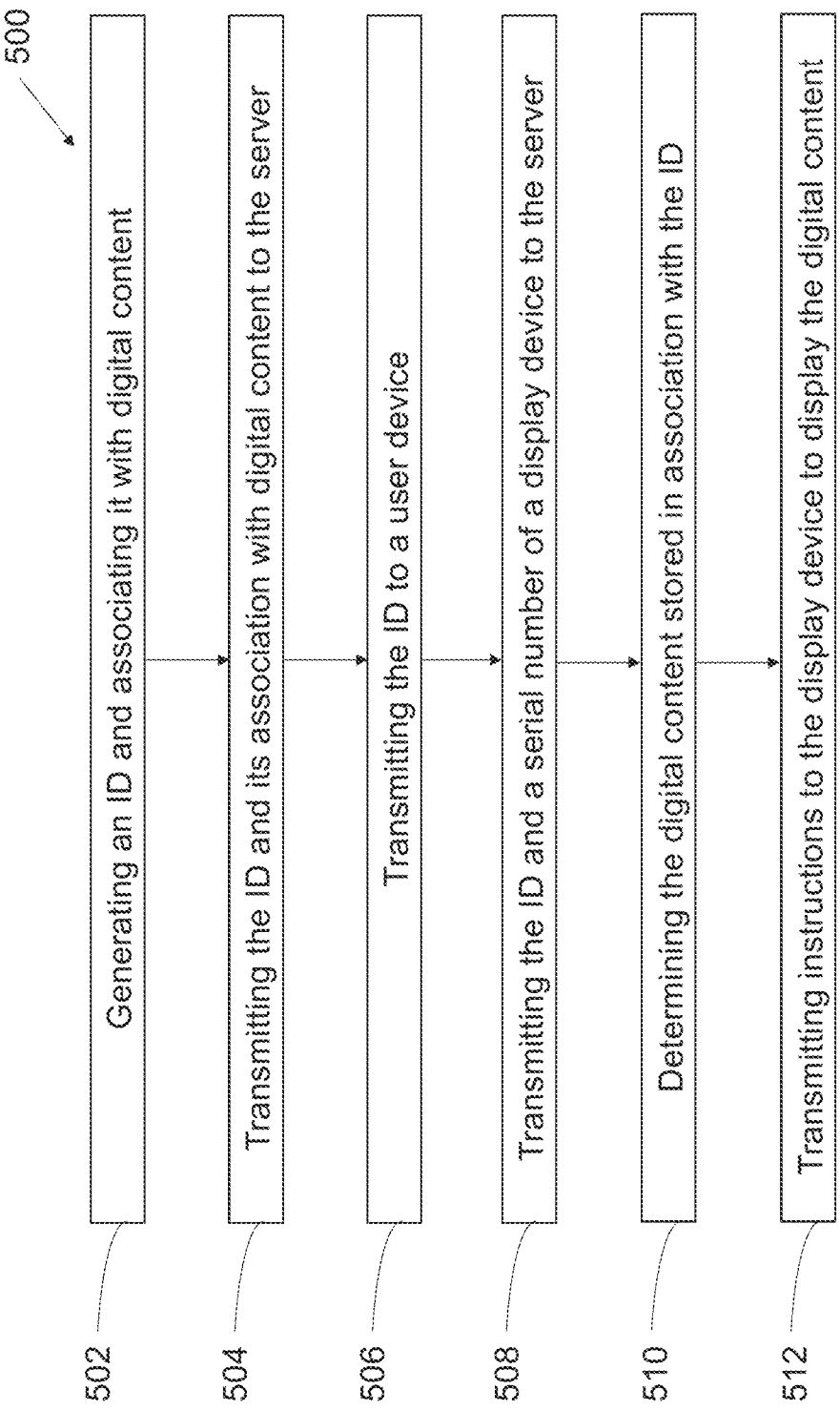
FIG. 8 is a method flow diagram.

More specifically, the server 204 may initiate display of the digital content by sending instructions to the display device 202 to display the digital content, as set out in FIG. 8. Alternatively, the display device may poll the server for assigned digital content. The display device displays the digital content to the subject, records the results, and transmits these to the server, as set out in FIG. 3. The administrator and user device 208 are used for pairing a display device to a test patient, as set out in FIG. 8. The administrator device is used to assess the results from FIG. 3, as set out in FIG. 9.

Figure 3:
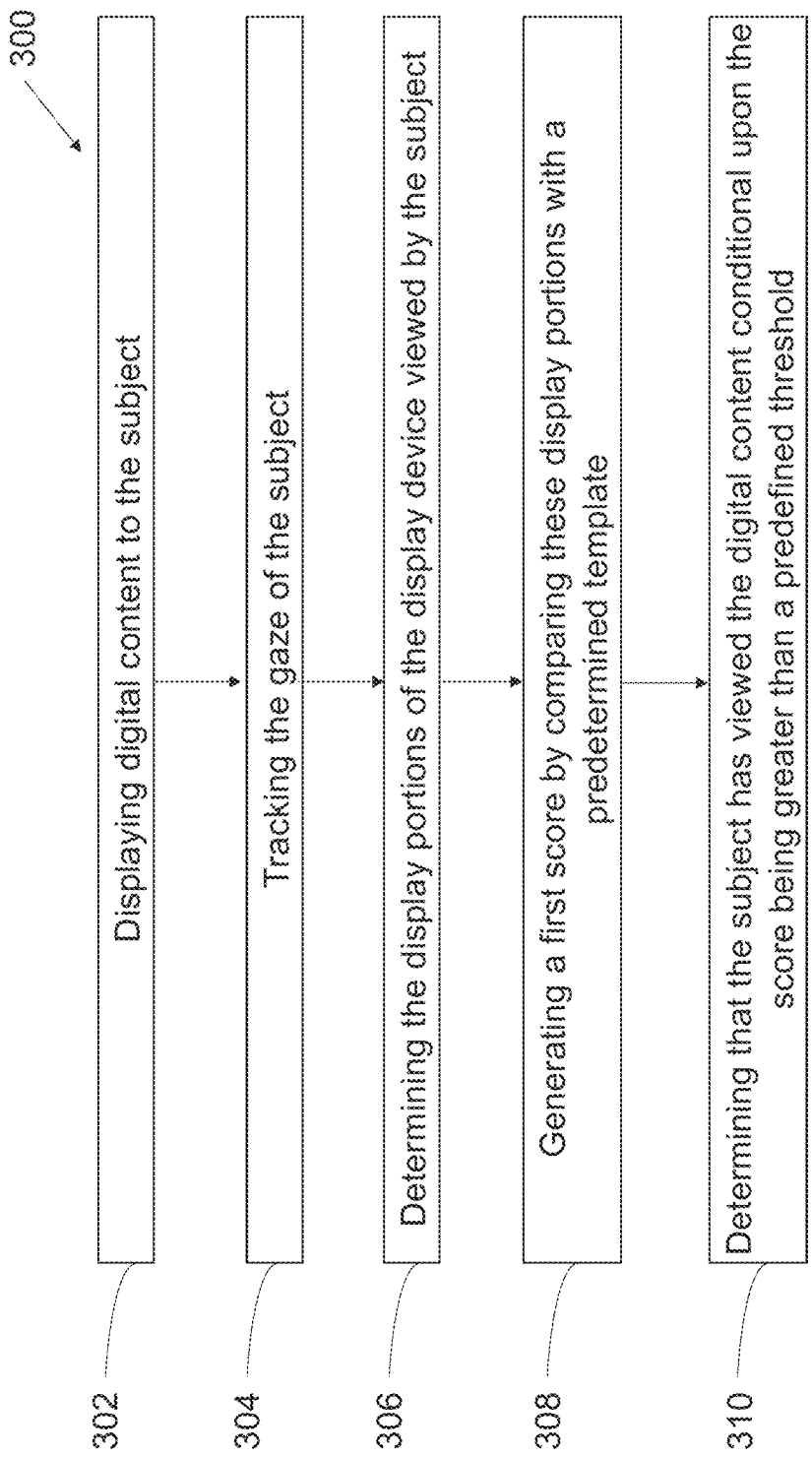
FIG. 3 is a method flow diagram.

FIG. 3 shows a method of determining whether digital content has been viewed by a subject. The method provides an improved and objective measure, based on gaze tracking, from which it can be determined whether the subject has viewed the digital content.

In step 302, digital content 104 is displayed to the subject using a display device 202. In the example shown in FIG. 1, the digital content is displayed in a VR headset 106. Other display devices are possible, for example, AR headsets, XR headsets, smartphones, computers, tablets, projector systems and the like. The digital content may be displayed in an augmented reality, virtual reality, or mixed reality environment.

In an example, the digital content 104 comprises a video. The video depicts, for example, a medical procedure being carried out and describes the effects, risks and benefits of that procedure. Optionally, audio content is played over the video during display step 302. The display device 202 can include a speaker for this purpose. Whilst in an embodiment the content 104 is a video, the invention is not so limited and other forms of displayed content are envisaged, including static images or slide shows, with or without audio. In particular, the content may comprise a virtual scene, possibly interactive. A virtual scene may be recorded; some or all of a virtual scene may be rendered in real time, similar to the video, but without pre-rendering. The virtual scene may allow the subject to move around or at least translate a head position.

In step 304, the gaze of the subject is tracked whilst the digital content 104 is being displayed in step 302. Step 304 can be performed for the entire duration of step 302 or for a temporal portion thereof. That is, step 304 can be performed for only part of the duration of the digital content 104.

The process of eye or gaze tracking is known to the skilled reader, per se. It is sufficient here to state that the gaze of the subject can be tracked over time by monitoring for changes in light (e.g., infrared) reflected from particular features of the eye (e.g., corneal reflections or the centre of the pupil). One or more illumination sources for illuminating the subject's eyes and one or more camera sensors for detecting the reflected light are arranged relative to the subject for this purpose. The illumination sources and/or camera sensors can be built into the display device 202 or provided separately to the display device 202.

Optionally, tracking the gaze of the subject 102 includes monitoring a head position of the subject whilst the digital content 104 is being displayed. Methods of monitoring head position and its effects on the gaze direction are known to the skilled reader, per se.

The use of a VR or AR or XR headsets 106 for displaying digital content is particularly advantageous because head movement causes little, if any, relative movement with the display screen mounted in the display device 202. In general, therefore, the portion of the display device and hence the content portion viewed by the subject at any instance in time depend on eye position only. However, if the digital content extends across multiple fields of view, then the content portions viewed by the subject can vary with head position, even though the portion of the display device being viewed by the subject may remain unchanged. XR, VR and AR headsets can include one or more in-built motion sensors, such as accelerometers or gyroscopes, to monitor head movement for this purpose.

XR, VR and AR headsets 106 are also especially suited for performing steps 302 and 304 because they include in-built illumination source(s) and camera sensor(s) which are arranged comparatively closer to the eyes of the subject, as compared with other display devices, such as smart phones. Hence, the signal-to-noise ratio of the reflected signal captured in step 304 is relatively high, for a given source and sensor specification.

Moreover, the arrangement of and the orientation between the illumination sources, camera sensors and the eyes of each subject is fixed when using a VR, XR, or AR headset. This simplifies processing.

In step 306, the display portions of the display device 202 viewed by the subject during display step 302 are determined through the gaze of the subject. The display portions comprise a pixel or cluster of pixels. The process of determining these display portions from a gaze direction is known to the skilled reader, per se. Step 306 is performed by the display device. It is noted that, the subject may view, per frame of displayed digital content, a plurality of pixels or pixel clusters, depending on the frame rate of the digital content and camera sensors (the natural frame rate of the eye is around 30-60 Hz).

In an embodiment, the total number of times the subject views particular display portions over the duration of display step 302 or a temporal portion thereof can be recorded, for example, in a matrix. The matrix may have dimensions equal to, or less than, the pixel dimensions of the display device, and is initially empty (i.e., full of 0s). The values stored in the matrix are incremented if it is determined that the corresponding pixel index of the display device has been viewed by the subject. The matrix which results, can be visualised as a heat map. It shows the total number of times the subject has viewed particular display portions of the display device.

Alternatively, the total number of times the subject views particular display portions is recorded in a matrix for each frame of the digital content or temporal portion thereof. The method for recording this information into the matrix is substantially the same as described above. The difference, however, is that a separate matrix is generated for each frame of the digital content. The matrices therefore form a set, with each matrix representing a time instance of the digital content. It will be appreciated that these matrices can be consolidated into a unitary matrix of higher dimension. The matrix set is a map from which it can be determined which content portions were viewed in display step 302.

In step 308, a first score is generated by comparing the display portions determined in step 306 with a predetermined template. The predetermined template comprises a map of a model subject's gaze over the duration of the display of the digital content. The predetermined template may be representative of the model or ideal subject having viewed the digital content adequately or diligently.

The generated template may be a heat map showing the total number of times the model subject views particular display portions of the display device over the duration of display step 302 or a temporal portion thereof. Alternatively, the template may be a matrix set, showing the total number of times the model subject views particular display portions for each frame displayed in step 302 (or a temporal portion thereof). Furthermore, a plural number of representative subjects results may be used and "averaged" or otherwise amalgamated to form a single ideal template result.

In an example, the display device 202 performs step 308 and transmits the first score and the map to the server 204 for storage. Conveniently, the display device 202, after step 304 or step 306 of FIG. 3, sends or uploads the gaze tracking data acquired in step 304 to the server and subsequent steps are performed at the server 204. Any of steps 306 to 310 can be performed either at the display device or the server.

In an example, the first score is calculated as a Sobolev norm, e.g., the $h_{-1}$ Sobolev norm. The equation for calculating the $h_{-1}$ Sobolev norm, $d(A, B)^2$, is shown below.

$$d(A, B)^2 = \sum_k \frac{F(A-B)_k^2}{1 + (2\pi|k|)^2}$$

Where A, B are the matrices, $F(A-B)_k$ is the Fourier coefficient of wavevector k.

The Sobolev norm is especially effective for this method because fine-scale differences between the maps have much less effect on the calculated score than coarser-scale differences between the maps. As such, the Sobolev norm is effective at eliminating any variances which exist between how different subjects view digital content. Other methods for calculating the first score in step 308 are, however, possible.

If the predetermined template is a heat map, step 308 comprises generating a single Sobolev norm. The approach of consolidating the display portions viewed in step 306 into a heat map improves the computational efficiency of step 308. If the predetermined template is a set of matrices, step 308 comprises generating a Sobolev norm for each corresponding time instance. That is, a Sobolev norm for each frame of the displayed digital content is calculated. Using this approach, it is also possible to determine whether the subject has viewed the appropriate content portions at the appropriate time.

As such, the first score generated in step 308 may be a single value or a plurality of values. A single value can, however, be derived from the plurality of values, for example, through averaging.

If the map generated in step 306 relates to a temporal portion of the digital content, the corresponding temporal portion of the predetermined template is used for generating the score in step 308.

In another embodiment, gaze points of a subject from start to end point are recorded, and compared with a template recording. The template recording may be an actual recording of, for example, a volunteer test subject, or a composite template, which is derived by "averaging" of the results of actual previous recordings.

The gaze of the subject is recorded continuously (for example on a frame-by-frame basis) during the playback of digital content. For each timestamp, a 2D vector (u,v) is stored together with the timestamp, where u denotes the horizontal position (e.g., a pixel column) and v denotes the vertical position (e.g., a pixel row) of the display device. In the following, ground truth (best) denotes the optimal (model) recording of gaze data set for a specific video content, while measured (mes) gaze data denotes the recorded gazes of a subject for the same digital content (e.g., video). Thus, measured relates to the current subject results and ground truth relates to a template recording.

Figure 5:
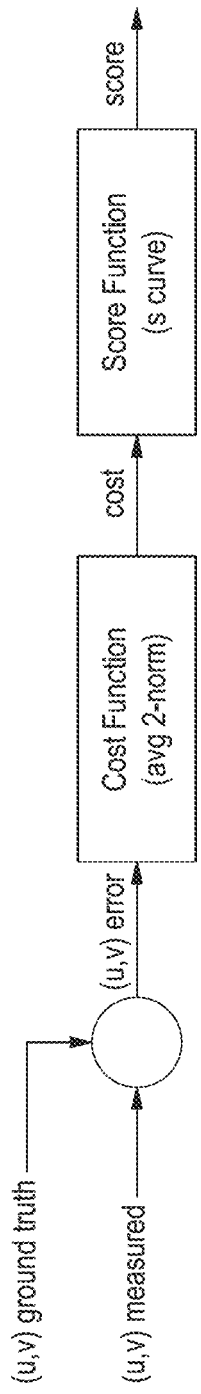
FIG. 5 is a flow chart of an example method.

Referring now to FIG. 5, a data processing scheme for generating the score in step 308 is illustrated.

As noted above, the ground truth and measured gaze data sets comprise a list of 2D vectors (u, v) for each timestamp of the digital content being displayed. For a video, the timestamp corresponds to a particular frame. Before generating the score according to the scheme illustrated in FIG. 5, data cleaning is performed. Data cleaning is important as it has been found that the eye-tracking sensor hardware (especially those built into XR, AR and VR headsets) cannot reliably sample without error. For example, over the course of a minute or more, current sensors tend to fail to acquire at least one data point in the measured or ground truth data sets. As a result, the measured and ground truth data sets may not sample the same time domains and, in particular the measured data set may sample a subject's gaze at a timestamp which the ground truth data set has not.

To address this problem, data cleaning may include discarding measured gaze data, which has been acquired at a timestamp (e.g. relating to a frame, j, of a video), for which the ground truth data has no counterpart. That is, where the ground truth data set has no 2D vector (u, v) at that timestamp. Moreover, if the measured gaze data set samples less than a predetermined fraction of the timestamps of the ground truth data set, then the score is set to 0 (i.e. the lowest value) to indicate that the subject has not viewed the digital content.

In a specific example, the predetermined fraction is 0.05. For video content, this ensures that there is at least one sampling point per second (assuming the video frame rate is around 20 Hz). In some examples, the predetermined fraction is greater and may take a value of: 0.10, 0.20, 0.30, 0.40, 0.50, 0.60, 0.70 or 0.80, or more generally be in the range 0.05 to 0.80. The skilled reader will understand that the value of the predetermined fraction can be adjusted according to the needs of the system. For example, fewer discards are expected with more reliable eye-tracking sensors, and so the predetermined fraction can then be comparatively greater in value.

Turning back to FIG. 5, in a first step, an error value is computed based on the ground truth (i.e. the predetermined template for a given temporal portion of the digital content) and the measured gaze data sets (i.e. the display portions viewed by a test subject in that temporal portion). The error represents the magnitude with which the ground truth and measured gaze data differ. A greater error denotes a test subject that has paid less attention to the digital content being displayed (or rather paid less attention to the salient points of the digital content), whereas a lower error denotes a test subject that has paid more attention to it. The error can be computed as an L2-norm. For example, the error value can be calculated for each measured gaze data and ground truth data point in the data set (i.e. for each timestamp in the measured data set). The error value is then a list of the respective error values for each timestamp. Alternatively, the error value can made into a single value by summing all the calculated L2-norms.

In a second step, a cost value for the ground truth and measured gaze data sets is computed. The cost value can be computed by averaging all the error values in the list of error values, or equivalently, if the error value is a single value by dividing through by the total number of timestamps in the measured gaze data set. The cost value, which is output by the cost function, is unbounded in that it can assume any positive value.

In a third step, the cost value is transformed into a bounded range, for example a score between 0 and 10. The skilled reader will understand that the values of the upper and lower bound are arbitrary in that the upper bound can assume any value. The score can also be translated into other descriptions, for example a simple pass fail or any other gradation. This is achieved by labelling different bounded score ranges. For example, names can be given to groups of scores, such as for example if the bounded score range is 0 to 10: scores of 0 to 3="fail", scores of 4 to 6="partial pass or fail", scores 7 to 10="pass". Different actions may be taken depending where on the scale the subjects score falls.

An example of a cost function is the average 2-norm (i.e. L2-norm) of the distance of the measured gaze ($u_{mes}$, $v_{mes}$), relative to the ground truth ($u_{best}$, $v_{best}$). More concretely, the average 2-norm between the ground and measured gaze data over time stamps $\{n_0, n_1, n_2, \ldots, N\}$ is calculated according to Equation 1:

$$\text{cost} = \frac{\sum_{n_0}^{n=N} \sqrt{(u_{best}[n] - u_{mes}[n])^2 + (v_{best}[n] - v_{mes}[n])^2}}{N} \quad \text{Equation 1}$$

Where u[n] is the horizontal and v[n] is the vertical position for sample number n, N is the total number of timestamps or sampling points of the measured gaze data and $n_0$ is the first sampling point or the earliest timestamp. The numerator denotes the single error value, which can be computed in the first step of FIG. 5.

The cost value (higher is worse, quasi no upper bound) can be transformed to a bounded score (higher is better) using a sigmoid function of the form shown in Equations 2 or 3.

$$\text{Score} = s_{max}\left(1.0 - \tanh\left(\frac{\text{cost}}{\text{cost}_{divider}}\right)\right) \quad \text{Equation 2}$$

wherein, $s_{max}$ is the maximum score (i.e. the upper bound, such as 10), tanh is the hyperbolic tangent function and $\text{cost}_{divider}$ is a tuning value that is calibrated for a given video (or other form of digital content) and ground truth.

$$\text{Score} = 0.5 s_{max}(1.0 - \tanh(\text{cost} - thres)) \quad \text{Equation 3}$$

wherein, $s_{max}$ is the maximum score (i.e. the upper bound, such as 10), tanh is the hyperbolic tangent function and thres is a threshold tuning value which is calibrated for a given video (or other form of digital content) and ground truth.

A maximum score indicates that the test subject viewed, within the error of the system and data processing scheme, the same display portions as the model subject. That is, the display portions viewed by the test subject are the same as those in the predetermined template.

Any convenient means of converting the result of the cost analysis into a score may be used. The cost function could be used in its raw form but it might be unwieldy, for example in terms of conveniently displaying.

A score may be computed for one or more temporal portions of the digital content. The bounded scores allow the results to be easily presented in the form of a graph, with any degree of granularity that might be desirable. The form of the displayed content may suggest having different degrees of granularity for different temporal portions of the displayed content. A final score can then be calculated by taking a weighted average of the scores for each temporal portion. The weights can be determined based on the length of the temporal portions (i.e. a period of time) and/or based on a perceived importance or priority of each temporal portion. For example, if the digital content relates to a medical procedure, then the temporal portion in which the risks of the medical procedure are described may be labelled as "high" importance. The weights increase as the relative length of the temporal portion increases and as the perceived importance of the temporal portion increases. For example, for mixed content including static presentations as well as video, less detail may be required for the static portion and accordingly the weight of the score corresponding to the static portion of the digital content is comparatively lower. Alternatively, portions of the displayed content may of higher priority and require greater granularity When displaying the scores or representing the scores the raw data can be combined in any convenient way, for example if a relatively low degree of granularity is required the scores of a plurality of frames or timestamped point may be combined and an average taken. Alternatively, a lowest score or highest score can be taken to represent the scores of the plurality of time points for the time period being represented.

In order to generate the predetermined template, a robust ground truth is required in order for the output to provide a meaningful score. Multiple ground truth recordings for the same video can be combined, to form a more robust ground truth. For instance, they can be averaged (as shown in Equation 4), or used to define a band (range of display positions at each time point) in which gaze trajectories can lie, resulting in a cost of zero while in the band. The multiple ground truth data sets acquired can also be used to form a time band. A time band is a time domain, which the ground truth recordings collectively sample. For example, if two ground truth recordings are made with time domains $\{t_0, t_2, t_4\}$ and $\{t_1, t_3, t_5\}$, then the time band is the time domain $\{t_0, t_1, t_2, t_3, t_4, t_5\}$.

$$x_{best}[n] = \frac{\sum_{i=0}^{i=I} x_{best,i}[n]}{I} \quad \text{Equation 4}$$

where x[n]=[u[n], v[n]] is the vector of the horizontal and vertical gaze u[n] and v[n], at time point n, and $x_{best,i}$ is the i-th ground truth in a collection of I ground truth recordings.

Figure 6:
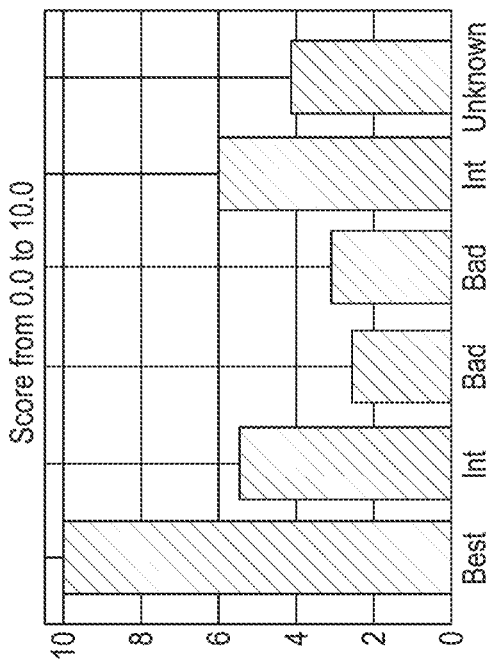
FIG. 6 is a graph of experimental results.

FIG. 6 shows the scores computed, according to the data processing scheme of FIG. 5, with the sigmoid function as expressed in Equation 2. In the experimental example, a total of six eye tracking recordings were collected by a single, male subject. All recordings with a score greater than a predetermined threshold (taken as 5 here) are considered to demonstrate that the subject has been sufficiently attentive during the display of the digital content. Scores less than this predetermined threshold indicate the subject has not been sufficiently attentive. As shown in FIG. 6, one is labeled as ground truth (best case), two as examples of 'bad' visual attention cases, two as example of 'intermediate' (int) cases and one is 'unknown' but likely a case of 'intermediate' attention. One problem with the sigmoid function of Equation 2, as shown in FIG. 6, is that it outputs some scores that are close to the predetermined threshold. The risk of false positives or false negatives is, therefore, relatively high. This means that the digital content may need to be redisplayed to a test subject, which wastes time and computational resources.

This is essentially because the tuning value depends strongly on the accuracy of the model subject's cost value. For example, if the model subject does not properly pay attention to the digital content being displayed, then the tuning value may be too low and false positives may be introduced.

Figure 7:
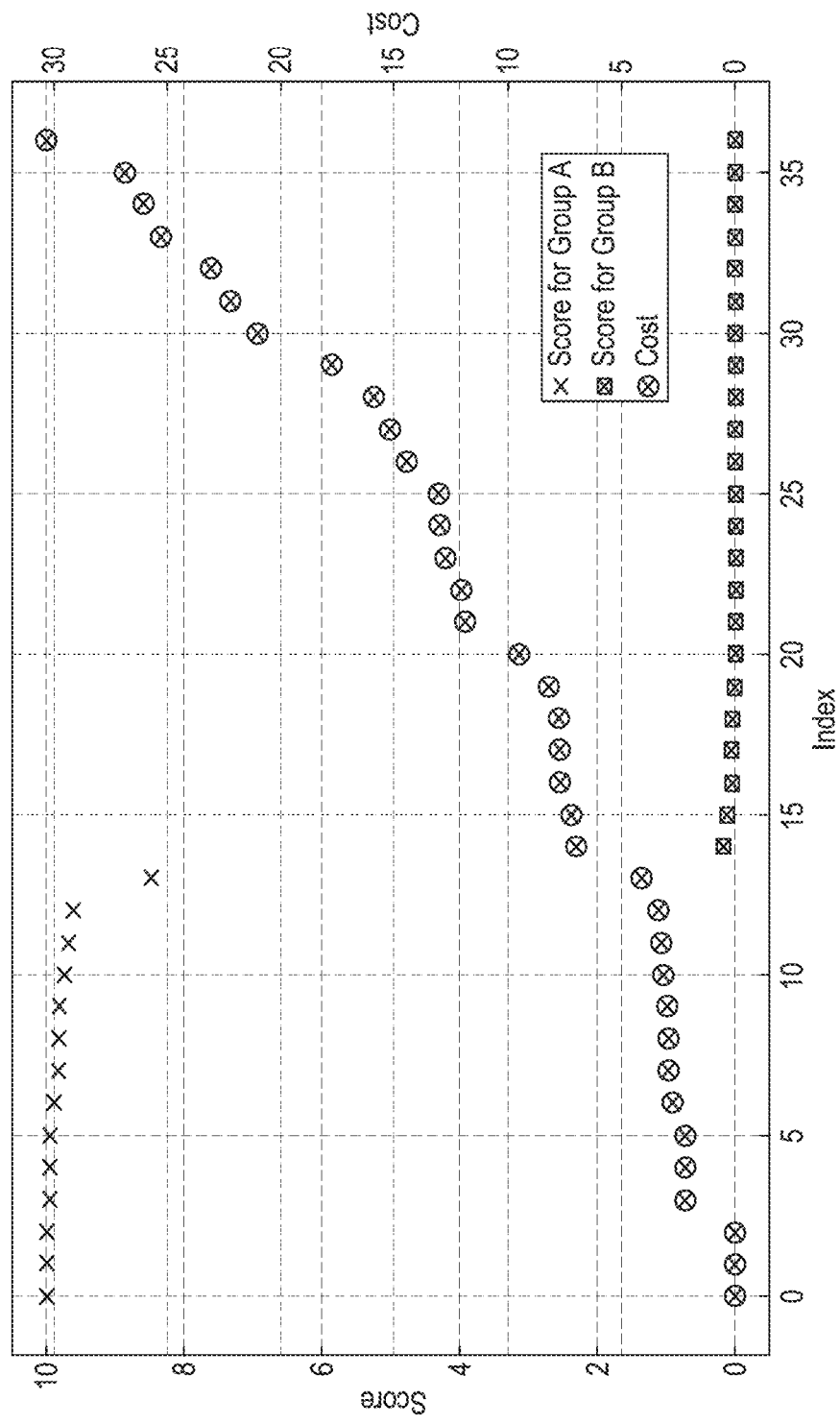
FIG. 7 is a graph of experimental results.

FIG. 7 shows the scores computed, according to the data processing scheme of FIG. 5, with the sigmoid function as expressed in Equation 3. In the experiment, a total of 37 eye tracking recordings were collected. The model subjects were split into two groups. A first group (denoted Group A), who were instructed to view the digital content attentively, and a second group (denoted Group B), who were instructed to not view the digital content attentively. Group A corresponds to the recordings indexed 0 to 13. Group B corresponds to the recordings indexed 14 to 36.

The tuning value, thres, in Equation 3 was determined as the average between the greatest cost value from Group A and the smallest cost value from Group B. In the specific example shown, the tuning value is around 5.5. In other examples, the tuning value could be set as the greatest cost value from Group A (i.e., around 4.5 in FIG. 7) or as the lowest cost value from Group B (i.e., around 6.5 in FIG. 7).

This approach is robust because it is less likely for a model subject to view digital content attentively (when they have been told not to) than vice versa. This is advantageous because the tuning value, thres, can then be determined more accurately, as it depends on the lowest cost value from Group B. The resulting sigmoid function is highly effective at delimiting between test subjects that have viewed the digital content attentively (i.e. have a score greater than a predetermined threshold, set to 5 in FIG. 7) and those that have not.

Returning to FIG. 3, in step 310, it is determined that the subject has (sufficiently) viewed the digital content (or temporal portion thereof) conditional upon the first score being greater than a predefined threshold.

The comparison between the first score and the predefined threshold can be determined locally by the display device. Alternatively, the maps determined in step 306 can be transmitted to the server 204 for carrying out steps 308 and 310.

If the first score comprises a plurality of values, there may be a respective predefined threshold for each score value. That is, a predefined threshold for each frame of the digital content. By comparing these respective score values and thresholds it can be deduced whether and which temporal portions of the digital content have not been viewed. These temporal portions can then be selected for redisplay, as set out in optional step 312.

If the first score generated in step 308 is based on a temporal portion of the digital content, step 310 may be further conditional upon the temporal portion of the digital content being greater than 50%, 60%, 70%, 80%, 90%, or 95% of the duration of the digital content.

In optional step 309*a* (not shown), one or more questions are displayed to the subject via the display device 202. The one or more questions can be displayed concurrent with, or sequential to the carrying out of steps 302 to 308. The questions concern the digital content being displayed and hence test that the subject has viewed and processed the digital content that has been, or is being, displayed to them. The display device provides a means for inputting a response to the questions and a means for recording these inputs. In an example, the input means is a microphone and the recording means a storage medium. Other input means are possible.

In optional step 309*b* (not shown), a second score is generated based on the input received from the subject following step 309*a*. The second score is indicative of the subject having answered the questions correctly. In an example, the second score is the fraction of questions answered correctly. The second score can be calculated locally using a processing unit built into the display device 202. Alternatively, the inputs received by the display device are transmitted to the server 204, which calculates the second score. The one or more questions displayed are stored at the server 204 in advance.

The carrying out of step 310 may be further conditional on the second score being greater than a second predefined threshold. As has already been noted, the second predefined threshold is indicative of the subject having answered the one or more questions correctly. In an example, the second predefined threshold is in the range 0.7 to 1 and the second score is a fraction of questions that were answered correctly.

Optionally, in step 312 (not shown), the digital content or the temporal portion thereof is replayed to the subject. Following step 312, the method restarts at step 304. Step 312 is carried out if the first or second score is less than the first or second predefined threshold, respectively. Replaying the temporal portion of the digital content which the subject has been determined not to have viewed, as opposed to all of the digital content, is advantageous because the computational expense of steps 304 to 308 is reduced.

Figure 4:
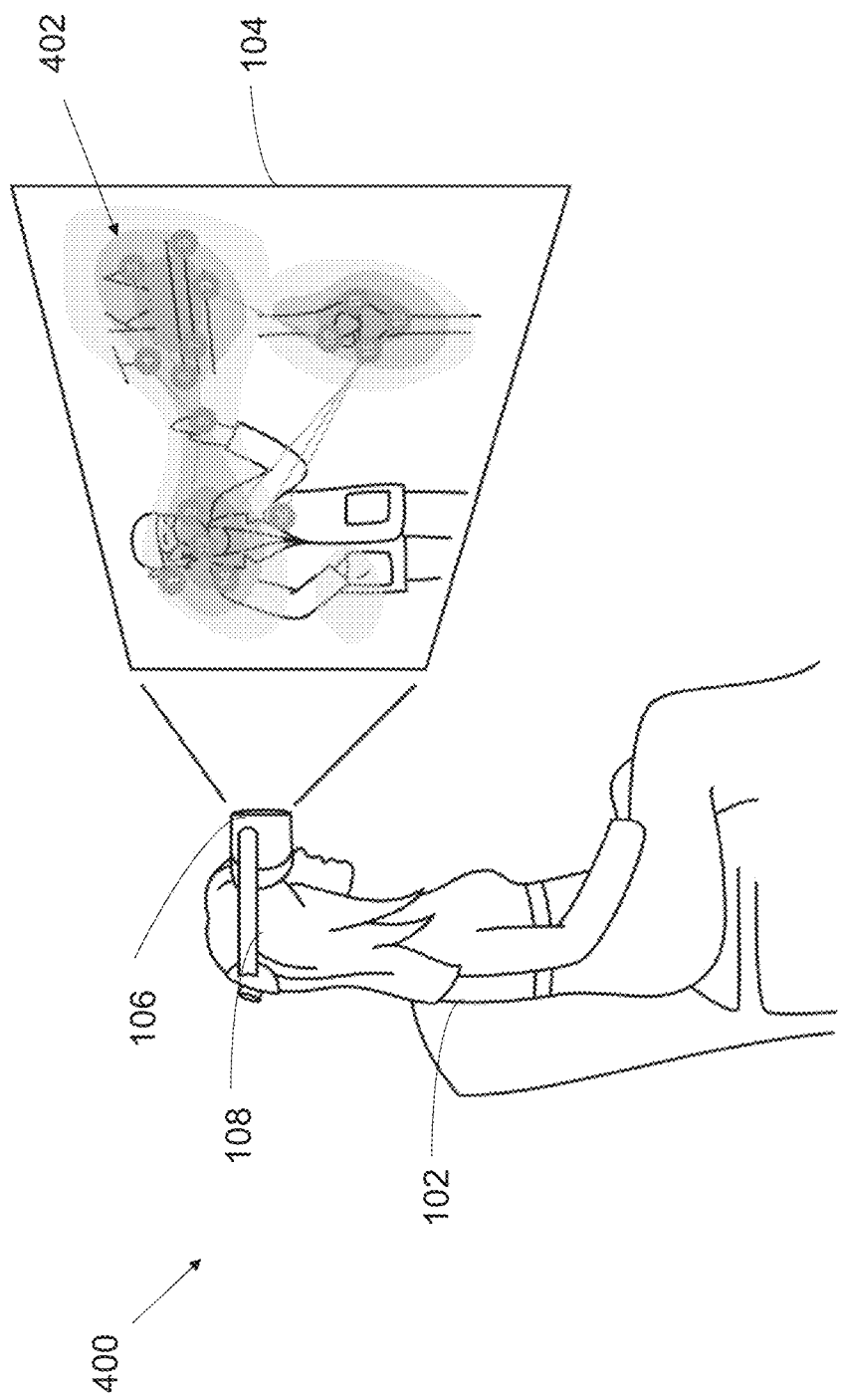
FIG. 4 is a schematic illustration of the recorded gaze of the subject and a heat map, showing the display portions viewed by the subject during display of the digital content.

FIG. 4 is a schematic illustration showing a visualisation of the heat map generated in step 306 for digital content 104. The mapping shown is a heat map 402 showing the frequency that the subject has viewed particular portions of the display screen (in other words the numbers represent the gaze plot path, i.e. the chronological order of recorded gaze points. The heat map is shown overlaying a content portion of the digital content displayed in step 302. As with FIG. 1, the projection of the digital content and heat map is for illustrative purposes only.

FIG. 8 is a flow chart of a method of pairing a display device 202 to the subject. Pairing of the display device to the subject ensures that the appropriate or correct digital content is subsequently displayed to them (e.g., in FIG. 3). The method of FIG. 8 may be implemented using a web application, which is accessible by the administrator device 206 and/or the user device 208. The web application may be hosted by server 204.

In an example, when an administrator creates a new case, the administrator selects a display on which a particular media content will be shown. The ID of the case (case or subject ID), the content ID, and the ID of the display device may be stored on the server 204.

In an example method, the server 204 receives a request (for example from the administrator device 206) and generates a case ID. In an example, the case ID is a random string comprising alphanumeric characters. The case ID can be generated without receiving any patient data or other forms of personal data relating to the subject. The server 204 transmits the case ID to the administrator device 206. The administrator device 206 associates the case ID with a specific item of digital content and a specific display device (using a display device ID e.g. a serial number). The administrator device 206 transmits at least (information regarding) the case ID, the associated content, and serial number of display device to the server 204. The associated content may be stored on another device for example and the server 204 only needs to know the association information and the location. But the server 204 may store all the information. The display device 202 (which may be one of a plurality of display devices) may poll the server for content associated with its serial number. On initiation of a media content display, for example, when the server 204 is polled by a display device 202 for which it has associated content, the server 204 transmits the associated content or instructions for acquiring the associated content to the display device 202 for viewing by a subject of the display device 202. The server 204 may instead push the content to the display device after an initial handshaking operation.

In step 502, an identifier (ID) (case ID) is generated in the server and associated with digital content by the administrator device. The ID may uniquely define the subject for example. In an example, the case ID is a random string comprising alphanumeric characters. Preferably, for data security purposes, the case ID is generated without the use of any personal data associated with the subject. Step 502 may be performed by the administrator device 206 or user device 208.

In step 504, the case ID and the association between the digital content and the case ID is transmitted to the server 204 for storage. Step 504 is performed by the administrator device 206. Optionally, step 504 further includes transmitting the digital content to the server 204. Alternatively, the server 204 stores the digital content in advance and a digital content identifier is transmitted to the server instead.

In step 506, the ID is transmitted to, for example, a user device 208 or the administrator device 206. Step 506 may be performed by the server 204.

In an example, the ID is transmitted via a cellular network as a text message. The subject may provide or register their mobile number into the system for this purpose. Preferably, although not necessarily, the mobile number of the subject is deleted after the method steps of FIG. 8 are completed.

In an example, the administrator device 206 is operated for steps 502 to 506 using a web-based application. The text message optionally sent in step 506 may further include a link to the web-based application used by the administrator device in steps 502 to 506.

In step 508, the user device 208 transmits a serial number that uniquely defines a display device and the ID received in step 506 to the server 204.

In an example, the user operates the user device 208 and a display device 202 is assigned to them. In another example, the user selects a display device. The serial number can be obtained by scanning a 2D code printed on the display device. In an example, the 2D code is a Quick Response (QR) code, which encodes the serial number. Alternatively, the serial number itself is printed (unencoded) on the display device and can be read by the user directly from the display device.

In an example, the user provides the serial number and ID to the server 204 through a web-based application. The user may access the web application through a link provided to the user device 208 by the administrator device 206. The web-based application provides an input field for entering the serial number of the display device and the ID. If the user scans a 2D code on the display device 202 using a camera, the input field for the serial number is automatically filled with the serial number following processing of the 2D code.

In step 510, the server 204, in response to receiving the serial number and the ID, determines which digital content 104 should be displayed to the subject using the ID. This is possible because the server stores the ID and digital content (or digital content identifier) in association with one another, following step 504. Following completion of the method in FIG. 8, any association between the serial number of the display device and the ID can be deleted.

In step 512, the server 204 transmits instructions to the display device 202 corresponding to the serial number to display the digital content 104 associated with the ID. Optionally, step 512 further includes transmitting the digital content to the display device. Alternatively, the digital content is already stored on the display device and hence it does not need to be sent. The server may maintain a record of the digital content stored by each display device for this purpose. This completes the pairing process. The method described in FIG. 3 can proceed after pairing is complete.

The numbering of the method steps is not intended to limit the order in which those steps are performed. The steps can be performed in other working orders. For example, step 504 may take place after step 506 etc.

The administrator 206 and user device 208 may be the same device or any device running the web-application; both the assignment of content and the display device 202 may be performed on the same administrator or user device.

In another embodiment the administrator or user device is used for assigning the content, but a separate device subject device (not shown) is operated by the subject to assign the display device.

As the skilled reader will appreciate, the method of FIGS. 3 and 5 are not limited to being applied to any digital content in particular. The method of FIG. 3 advantageously quantifies, in an objective way, the extent to which a subject has viewed digital content. As has already been noted, this score can be used to determine whether a subject has viewed the digital content or not. The score can also be used as basis for performing other or additional steps or procedures.

One example use case is for educational or training purposes. In the education sector, it is a well-known problem that children have varying degrees of attention span. It is difficult, however, to objectively determine which children have the lowest attention spans and, more importantly, how long on average this attention span lasts. The approach in this disclosure provides a means for determining both which children have the worst attention spans (which is useful in of itself for teachers) as well as the length of their attention spans. The scores generated according to the method of this disclosure can also be used to complement testing of the content being taught. For example, if the training course relates to the use of machinery, the test subject may only be allowed to practice using the machine after the method determines that they have viewed the digital content sufficiently.

Another example use case is in a medical consent procedure, although there are a number of other use cases, as the skilled reader will appreciate. In the medical consent procedure scenario, the digital content relates to a medical procedure. The digital content may be a video which depicts the medical procedure being carried out, its effects, and the risks and effects of that procedure. The digital content may also include audio content. The ID referred to in FIG. 8 is then a case ID which is unique not only to the subject but also to the medical procedure.

The subject may be a patient requiring that medical procedure or a legal guardian to a person that requires that procedure. Before the medical procedure can be carried out, the subject and/or the legal guardian must consent to the medical procedure. Accordingly, following step 310, the subject and/or legal guardian may be provided with a medical consent form. The medical consent form can be displayed in the display device 202 or as a paper copy. This step is carried out if the first score generated in step 308 is greater than the first predefined threshold, and where applicable, if the second score generated in optional step 309*b* is greater than the second predefined threshold. The subject and/or legal guardian may then sign the medical consent form. The signature can be a digital signature input to the display device 202 or a wet ink signature. This process therefore facilitates the medical consent procedure.

Figure 9:
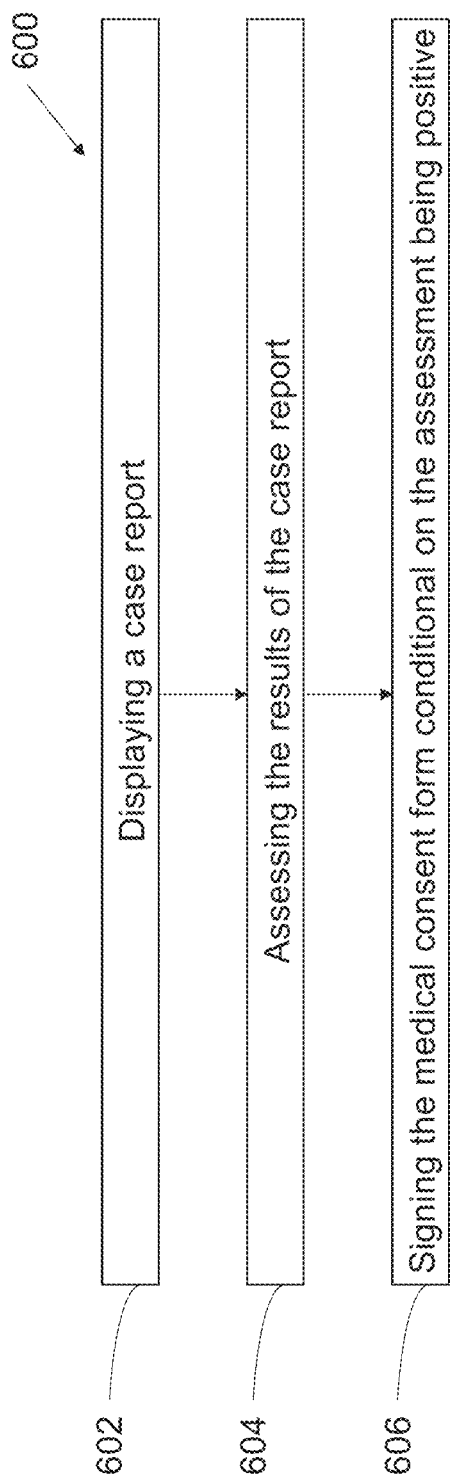
FIG. 9 is a method flow diagram.

FIG. 9 shows a method 600 in which a medical clinician or other qualified medical professional (a user) verifies the results generated in the method of FIG. 3 and proceeds with the medical procedure consent process on the basis of the results. The user may or may not be the same person as the administrator.

In step 602, a case report is displayed by a user or administrator device. The user or administrator device may be the same or different to the user or administrator devices 206, 208. In an example, it is a computer.

The case report may comprise the map generated in step 306, the first score generated in step 308, the second score generated in optional step 309*b*, the case ID generated in step 502, all the answers to the questions provided by the subject in optional step 309*a*, and the medical consent form digitally signed by the subject obtained in step 312. The details of these steps is not repeated here for conciseness. If the medical consent form is a paper copy, the medical consent form can be provided separately to the display device. The case report information can be downloaded from the server. The case report can be displayed in the web-based application used in FIG. 9.

In step 604, a user assesses the case report. The user may be a clinician or other qualified medical professional.

The assessment in step 604 comprises any one or more of the following: (i) verifying the correct case ID is associated with the subject; and (ii) verifying the first score(s) and/or second score are greater than their respective pre-defined thresholds. Optionally, the user further assesses the map displayed in the case report.

If the assessment in step 604 is affirmative, the user approves the consent of the subject and proceeds, in step 606, to sign the medical consent form. The medical consent form can be signed digitally, or, where a paper copy is provided using a wet-ink signature.

In some examples, the method of FIG. 9 is performed before step 312. In that case, the supervisor and user both digitally sign the medical consent form in step 606.

Figure 10:
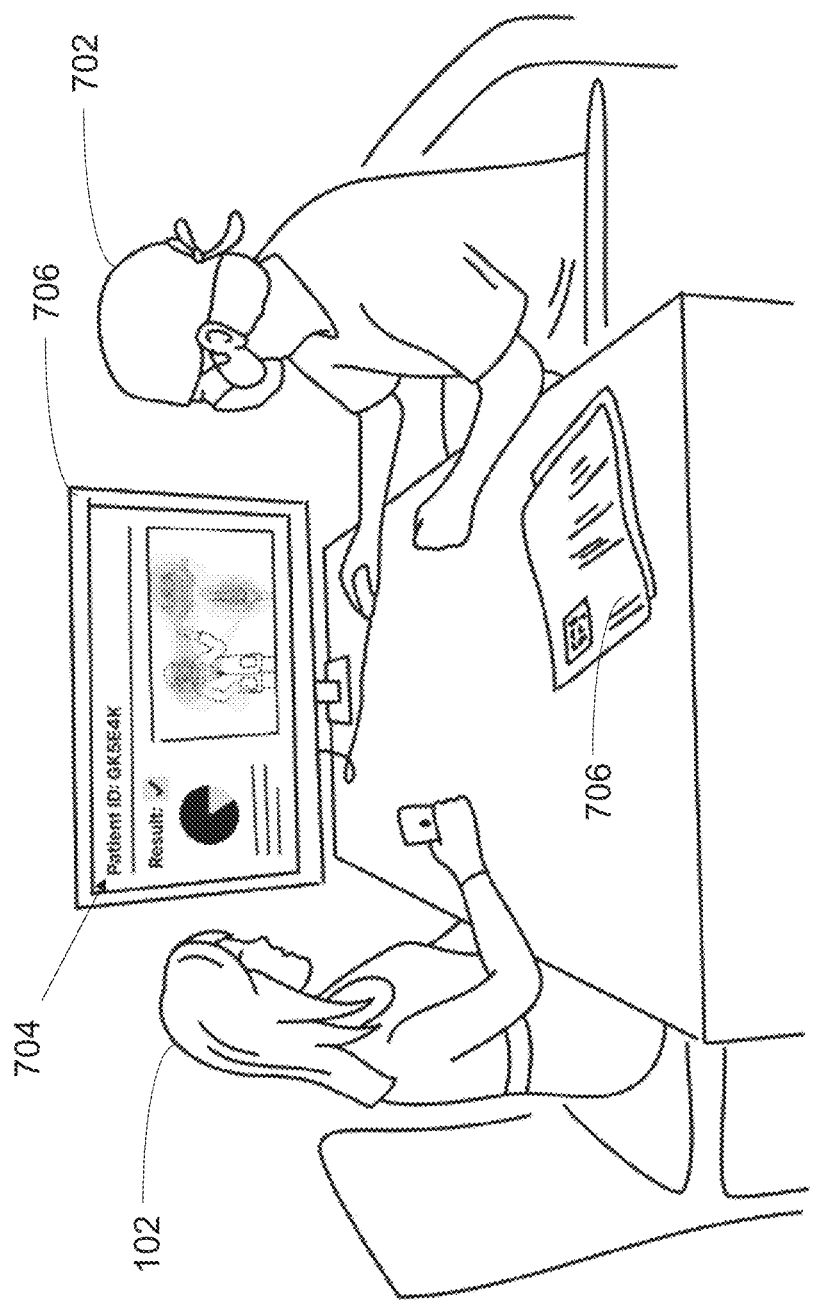
FIG. 10 is a schematic illustration of an administrator and a subject viewing a case report.

FIG. 10 is a schematic illustration of a clinician 702 and patient 102 viewing a case report 704 in a computing device 706. The medical consent form 708 is a paper copy, which the clinician 702 and test patient 102 subsequently sign following the verification procedure of FIG. 9.

Various modifications are possible within the scope of the invention, as will be clear to the skilled reader. For example, processing steps performed locally by the display device may instead be performed by the server. The subject may not necessarily be the person receiving the medical procedure. For example, the subject or test patient may be a parent or guardian of a child, who requires that medical procedure. Or, a person who has power of attorney over an individual legally incapable of making such decisions. The subject then provides consent on behalf of that other person. The medical procedure may relate to a clinical trial for a medicament or treatment arranged by a pharmaceutical company and is not limited to surgery. The user and administrator may be staff of the pharmaceutical company.

The invention claimed is:

1. A computer-implemented method of determining whether digital content has been viewed by a subject, the method comprising:
displaying, by a display device, the digital content to the subject;
tracking the gaze of the subject whilst displaying at least a temporal portion of the digital content to acquire tracking data;
determining from the tracking data, the display portions of the display device viewed in that temporal portion of the digital content;
generating at least one score by comparing these portions to a predetermined template of display portions for that temporal portion of the digital content; and
determining that the subject has viewed at least the temporal portion of the digital content based on the at least one score,
wherein the acquired tracking data comprises positional data related to the subject's gaze for each of a plurality of timestamped points, and
wherein generating a score comprises calculating an error value for each time stamped point by comparing the positional information at each timestamped point with corresponding positional data from the predetermined template.

2. The method of claim 1, wherein determining from the tracking data the display portions, comprises determining the display portions for each of multiple time points within the time period.

3. The method of claim 2, wherein generating a score by comparing comprises comparing at least a plurality of time points of the acquired tracking data with the corresponding points of the predetermined template.

4. The method of claim 1, further comprising generating the predetermined template by tracking a gaze of at least one model subject whilst displaying said digital content and acquiring the gaze tracking data.

5. The method of claim 1, wherein for each timestamped point that is present in the acquired tracking data and absent in the predetermined template: discarding the positional information related to the subject's gaze corresponding at said timestamped point.

6. The method of claim 1, wherein generating the score comprises calculating a cost value based on said error values.

7. The method of claim 6, comprising generating a bounded score from the cost value using a sigmoid function.

8. The method of claim 7, wherein a tuning value for the sigmoid function is determined based on a cost value calculated for a model subject that has been instructed, prior to viewing the digital content, to not view the digital content attentively.

9. The method of claim 1, further comprising:

transmitting, by a server, instructions to the display device to display the digital content responsive to the server receiving a first identifier defining the subject and a second identifier defining the display device, the method optionally further comprising:

transmitting, by the server, the digital content to the display device.

10. The method of claim 9, further comprising, before the digital content is displayed by the display device, the steps of:

selecting the display device for displaying the digital content;

scanning, by a subject device, a code provided on the display device, the code comprising or encoding the second identifier; and transmitting, by the subject device, the second identifier to the server.

11. The method of claim 9, further comprising, before the first identifier is transmitted to the display device, the steps of:

generating the first identifier;

associating the digital content to the first identifier; and transmitting the first identifier and at least the association between the digital content and first identifier to the server for storage.

12. The method of claim 1, wherein the display device is a virtual-reality, VR, or augmented-reality, AR, headset, and the gaze of the subject is tracked using sensors built into the VR or AR headset.

13. The method of claim 1, wherein conditional upon the score being greater than a predetermined threshold, the method comprises:

certifying that the subject is competent to consent to a process to which the digital content relates.

14. The method of claim 13, in which the process is a medical procedure.

15. The method of claim 1, wherein conditional upon the score being greater than a predetermined threshold, the method comprises:

certifying that the subject has successfully completed at least part of a training course to which the digital content relates.

16. A display device comprising:

a network interface for establishing wireless connections;

at least one processor coupled to the network interface; and a memory storing executable instructions, wherein the executable instructions are configured to manipulate at least one processor so that the method of claim 1 can be performed.

17. A system, comprising:

a server, comprising:

a first network interface for establishing network connections;

at least one first processor coupled to the first network interface; and a first memory storing executable instructions, wherein the executable instructions are configured to manipulate the at least one first processor; and a display device, comprising:

a second network interface for establishing network connections;

at least one second processor coupled to the second network interface; and a second memory storing executable instructions, wherein the executable instructions are configured to manipulate the at least one second processor to cause a method to be performed, the method comprising:

displaying, by the display device, the digital content to the subject;

tracking the gaze of the subject whilst displaying at least a temporal portion of the digital content to acquire tracking data;

determining from the tracking data, the display portions of the display device viewed in that temporal portion of the digital content;

generating at least one score by comparing these portions to a predetermined template of display portions for that temporal portion of the digital content; and determining that the subject has viewed at least the temporal portion of the digital content based on the at least one score, wherein the acquired tracking data comprises positional data related to the subject's gaze for each of a plurality of timestamped points, and wherein generating a score comprises calculating an error value for each time stamped point by comparing the positional information at each timestamped point with corresponding positional data from the predetermined template.

* * * * *